(12) United States Patent
Weber (10) Patent No.: US 8,734,829 B2
(45) Date of Patent: May 27, 2014

(54) MEDICAL DEVICES HAVING POLYMERIC NANOPOROUS COATINGS FOR CONTROLLED THERAPEUTIC AGENT DELIVERY AND A NONPOLYMERIC MACROPOROUS PROTECTIVE LAYER

(75) Inventor: Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 500 days.

(21) Appl. No.: 12/703,946

(22) Filed: Feb. 11, 2010

(65) Prior Publication Data

US 2010/0209471 A1 Aug. 19, 2010

Related U.S. Application Data

(60) Provisional application No. 61/152,492, filed on Feb. 13, 2009.

(51) Int. Cl.
| | | |
|---|---|---|
| *A61F 2/00* | (2006.01) | |
| *A61L 33/00* | (2006.01) | |
| *B05D 3/00* | (2006.01) | |
| *C23C 14/00* | (2006.01) | |
| *C23C 14/32* | (2006.01) | |

(52) U.S. Cl.
USPC ........... 424/423; 424/426; 427/2.1; 427/2.24; 204/192.15

(58) Field of Classification Search
USPC .......................... 424/423, 426; 427/2.1, 2.24; 204/192.15
See application file for complete search history.

(56) References Cited

U.S. PATENT DOCUMENTS

| | | | |
|---|---|---|---|
| 6,558,733 B1 | 5/2003 | Hossainy et al. | |
| 6,709,379 B1 | 3/2004 | Brandau et al. | |
| 6,740,077 B1 | 5/2004 | Brandau et al. | |
| 8,187,255 B2 * | 5/2012 | Weber et al. | 604/890.1 |
| 2001/0010022 A1 * | 7/2001 | Dauner et al. | 623/23.71 |
| 2004/0148015 A1 * | 7/2004 | Lye et al. | 623/1.15 |
| 2005/0070989 A1 | 3/2005 | Lye et al. | |
| 2005/0266040 A1 | 12/2005 | Gerberding | |
| 2006/0127443 A1 * | 6/2006 | Helmus | 424/423 |
| 2006/0129215 A1 | 6/2006 | Helmus et al. | |
| 2007/0224235 A1 * | 9/2007 | Tenney et al. | 424/423 |
| 2008/0188836 A1 * | 8/2008 | Weber et al. | 604/890.1 |

OTHER PUBLICATIONS

Ulbricht, "Advanced Functional Polymer Membranes," Polymer 47 (2006) 2217-2262.

Halme et al., "Charge transfer resistance of spray deposited and compressed counter electrodes for dye-sensitized nanoparticle solar cells on plastic substrates," Solar Energy Materials & Solar Cells 90 (2006) 872-886.

Budd et al., "Microporous polymeric materials," Materials Today 2004 40-43.

Budd et al., "Gass separation membranes from polymers of intrinsic microporosity," J. Membrane Sci. 251 (2005) 263-269.

\* cited by examiner

*Primary Examiner* — Abigail Fisher
(74) *Attorney, Agent, or Firm* — Fish & Richardson P.C.

(57) ABSTRACT

An implantable or insertable medical device is provided which contains the following: (a) a substrate, (b) a therapeutic agent-containable region disposed over the substrate, (c) a nanoporous polymeric layer disposed over the therapeutic agent-containable region and (d) a macroporous non-polymeric layer disposed over the nanoporous polymeric layer. The nanoporous polymeric layer largely regulates transport of species between the therapeutic agent-containable region and the exterior of the device. The macroporous non-polymeric layer has a larger pore size than the nanoporous polymeric layer and largely serves to isolate the polymeric material from surrounding tissue during in-situ delivery of the therapeutic agents.

20 Claims, 7 Drawing Sheets

MEDICAL DEVICES HAVING POLYMERIC NANOPOROUS COATINGS FOR CONTROLLED THERAPEUTIC AGENT DELIVERY AND A NONPOLYMERIC MACROPOROUS PROTECTIVE LAYER

RELATED APPLICATIONS

This application claims priority from U.S. provisional application 61/152,492, filed Feb. 13, 2009, which is incorporated by reference herein in its entirety.

TECHNICAL FIELD

This invention relates to therapeutic-agent containing medical devices, and more particularly, to medical devices having porous coatings which control therapeutic agent release.

BACKGROUND OF THE INVENTION

The in-situ delivery of therapeutic agents within the body of a patient is common in the practice of modern medicine. In-situ delivery of therapeutic agents is often implemented using medical devices that may be temporarily or permanently placed at a target site within the body. These medical devices can be maintained, as required, at their target sites for short or prolonged periods of time, in order to deliver therapeutic agents to the target site.

In some cases however, delivery of the biologically active material to the body tissue immediately after insertion or implantation of the medical device may not be needed or desired. For instance, if a stent is used to prevent the occurrence of restenosis after balloon angioplasty, it may be more desirable to wait until restenosis occurs or begins to occur in a body lumen that has been stented with a drug-coated stent before the drug is released. Therefore, there is a need for insertable or implantable medical devices that can provide delayed and/or controlled delivery of biologically active materials when such materials are required by the patient after implantation of the medical device. The in-situ delivery of therapeutic agents in a controlled manner often involves the use of a nanoporous material through which the therapeutic agents are transported.

Nanoporous materials have the potential to revolutionize drug delivery. For example, iMEDD, Inc. has created silicon membranes with parallel channels ranging from 4 to 50 nm. Diffusion rates of various solutes through such membranes have been measured and conform to zero-order kinetics in some instances (i.e., release is constant with time). This is in contrast with typical situations in which drug diffusion rates decay with time, because the concentration gradient, and thus the driving force for diffusion, is also decaying with time. One explanation for zero order behavior is that, by making the diameter of the nanopores only slightly larger than that of the drug, the nanopores act as bottlenecks, forcing the drugs to proceed in a substantially single-file fashion through the membrane. iMedd claims that the membranes can be engineered to control rates of diffusion by adjusting channel width in relation to the size of solutes. When the proper balance is struck, zero-order diffusion kinetics is possible.

Current techniques for the in-situ delivery of therapeutic agents in a controlled manner often involve the use of a polymeric nanoporous coating on the insertable or implanatable medical device to contain the agents and control their release rate. The polymeric coating, however, can sometimes cause an inflammatory response in the tissue with which it comes in contact. For instance, when a Drug Eluting Stent (DES) is implanted in a vessel, the inflammatory response can cause a reduction in the diameter of the vessel lumen within the stent. The inflammatory response can lead to late in stent thrombosis.

SUMMARY OF THE INVENTION

The above and other drawbacks of the prior art are addressed by the present invention in which implantable or insertable medical devices are provided which contain the following: (a) a substrate, (b) a therapeutic agent-containable region disposed over the substrate, (c) a nanoporous polymeric layer disposed over the therapeutic agent-containable region and (d) a macroporous non-polymeric layer disposed over the nanoporous polymeric layer. The nanoporous polymeric layer largely regulates transport of species between the therapeutic agent-containable region and the exterior of the device. The macroporous non-polymeric layer has a larger pore size than the nanoporous polymeric layer and largely serves to isolate the polymeric material from surrounding tissue during in-situ delivery of the therapeutic agents.

An advantage of the present invention is that medical devices may be provided, in which the transport of species into the medical device, out of the medical device, or both are tightly controlled, potentially displaying zero order kinetics.

Another advantage of the present invention is that the nanoporous polymeric layer may be formed from a wide range of polymers since, because of the use of a macroporous non-polymeric overcoating, it is not limited to a biocompatible polymer.

These and other embodiments and advantages of the present invention will become immediately apparent to those of ordinary skill in the art upon review of the Detailed Description and Claims to follow.

DETAILED DESCRIPTION

According to an aspect of the invention, medical devices are provided which contain (a) a substrate, (b) a therapeutic agent-containable region disposed over the substrate, (c) a nanoporous polymeric layer disposed over the therapeutic agent-containable region and (d) a macroporous non-polymeric layer disposed over the nanoporous polymeric layer. The nanoporous polymeric layer largely regulates transport of species between the therapeutic agent-containable region and the exterior of the device. The macroporous non-polymeric layer has a larger pore size than the nanoporous polymeric layer and largely serves to isolate the polymeric material from surrounding tissue during in-situ delivery of the therapeutic agents.

For example, a therapeutic agent may be transported from the therapeutic agent-containable regions such that it is released in vivo, an in vivo species may be transported into the therapeutic agent-containable region where it reacts with the therapeutic agent to form another species (e.g., a less detrimental or more beneficial species) which is then transported from the therapeutic-agent-containing region, and so forth.

The implantable or insertable medical devices of the invention may be configured to provide a therapeutic function beyond species transport, for instance, providing mechanical, thermal, magnetic and/or electrical functions within the body, among other possible functions. Consequently, medical devices in accordance with the present invention vary widely and include numerous implantable or insertable medical devices, for example, catheters (e.g., renal or vascular catheters such as balloon catheters and various central venous catheters), guide wires, balloons, filters (e.g., vena cava filters), stents (including coronary vascular stents, peripheral vascular stents, cerebral, urethral, ureteral, biliary, tracheal, gastrointestinal and esophageal stents), stent grafts, vascular grafts, vascular access ports, embolization devices including cerebral aneurysm filler coils (including Guglilmi detachable coils and metal coils), myocardial plugs, patches, pacemakers and pacemaker leads, left ventricular assist hearts and pumps, total artificial hearts, heart valves, vascular valves, anastomosis clips and rings, and other prostheses, including tissue engineering scaffolds for cartilage, bone, skin and other in vivo tissue regeneration, among others.

The medical devices of the present invention may be implanted or inserted within a variety of tissues or organs of a subject, including tumors; organs and organ systems including but not limited to the heart, coronary and peripheral vascular system (referred to overall as "the vasculature"), lungs, trachea, esophagus, brain, liver, kidney, urogenital system (including, vagina, uterus, ovaries, prostate, bladder, urethra and ureters), eye, intestines, stomach, and pancreas; skeletal muscle; smooth muscle; breast; cartilage; and bone. Preferred subjects (also referred to as "patients") are vertebrate subjects, more preferably mammalian subjects and more preferably human subjects.

Figure 1:
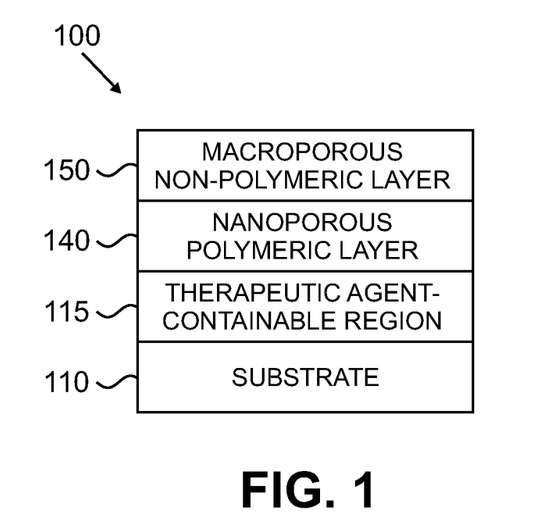
FIG. 1 shows a schematic cross-section through a portion of a medical device in accordance with an embodiment of the invention.

FIG. 1 shows a schematic cross-section through a portion of a medical device 100 such as those described above. The medical device include a substrate 110, a therapeutic agent-containable region 115 disposed over the substrate 110, a nanoporous polymeric layer 140 disposed over the therapeutic agent-containable region 115 and a macroporous non-polymeric layer 150 disposed over the nanoporous polymeric layer 140.

The substrate 110 may be formed in a wide variety of materials including (a) organic materials (e.g., materials containing 50 wt % or more organic species) such as polymeric materials and biologics (b) inorganic materials (e.g., materials containing 50 wt % or more inorganic species), such as metallic materials (e.g., metals and metal alloys) and non-metallic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, iron, niobium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic inorganic materials may be selected, for example, from metals (e.g., metals such as gold, iron, niobium, platinum, palladium, iridium, osmium, rhodium, titanium, tantalum, tungsten, ruthenium, and magnesium), metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N) and alloys comprising cobalt, chromium, tungsten and nickel (e.g., L605), alloys comprising nickel and chromium (e.g., inconel alloys), and alloys of magnesium and iron (e.g., their alloys with combinations of Ce, Ca, Zn, Zr and Li).

Specific examples of organic materials include polymers (biostable or biodegradable) and other high molecular weight organic materials, and may be selected, for example, from suitable materials containing one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

As previously indicated, the medical devices of the present invention contain one or more therapeutic agents (i.e., they may be used singly or in combination). The therapeutic agents may be present in pure form or admixed with another material, for example, a diluent, filler, matrix material, etc. Suitable materials for these purposes may be selected, for example, from suitable members of the polymers listed above, among many other possible materials. Where therapeutic agents are used in combination, one therapeutic agent may provide a matrix for another therapeutic agent.

By varying the concentration of the therapeutic agents, a range of therapeutic agent loading levels can be achieved. The amount of loading may be determined by those of ordinary skill in the art and will ultimately depend, for example, upon the disease or condition being treated, the age, sex and health of the subject, the nature of the therapeutic agent, and so forth.

"Biologically active agents," "drugs," "therapeutic agents," "pharmaceutically active agents," "pharmaceutically active materials," and other related terms may be used interchangeably herein and include genetic therapeutic agents, non-genetic therapeutic agents and cells. A wide variety of therapeutic agents can be employed in conjunction with the present invention. Numerous therapeutic agents are described here.

Suitable non-genetic therapeutic agents for use in connection with the present invention may be selected, for example, from one or more of the following: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, antimicrobial peptides such as magainins, aminoglycosides and nitrofurantoin; (m) cytotoxic agents, cytostatic agents and cell proliferation affectors; (n) vasodilating agents; (o) agents that interfere with endogenous vasoactive mechanisms, (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.).

Preferred non-genetic therapeutic agents include paclitaxel (including particulate forms thereof, for instance, protein-bound paclitaxel particles such as albumin-bound paclitaxel nanoparticles, e.g., ABRAXANE), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and suitable examples may be selected from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-a pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

In the medical devices of the present invention, transport of species is regulated by the nanoporous regions such as nanoporous polymeric layer 140 shown in FIG. 1. The pores of the release-controlling regions may be parallel to one another, they may be interconnected or both. They may be regular (e.g., cylindrical, etc.) or irregular in geometry.

Nanoporous regions for use in the present invention are not limited to any particular material and can be selected from a range of materials, including suitable members of the organic and inorganic materials listed above. Advantageously, however, the nanoporous region may be formed from a polymer material since such materials can be fabricated with specific pores sizes and with sufficient flexibility so that they are not prone to cracking or delamination when applied to a medical device substrate.

Figure 8:
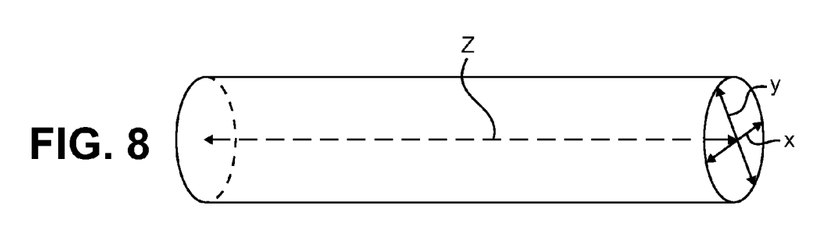
FIG. 8 is a schematic illustration of an idealized pore.

As used herein, a "nanoporous" region is one that contains nanopores. A "nanopore" is a void having at least one dimension (e.g., pore width) that does not exceed about 50 nm in length. Typically nanopores have at least two orthogonal (i.e., perpendicular) dimensions that do not exceed 50 nm and a third orthogonal dimension, which can be greater than 50 nm. By way of example, an idealized cylindrical nanopore is illustrated in FIG. 8. Being a nanopore, the cylindrical pore of FIG. 8 has at least one dimension (in this instance, the orthogonal dimensions "x" and "y," each of which correspond to the width of the nanopore) that does not exceed 50 nm in length. The third orthogonal dimension "z" of the cylindrical pore of FIG. 8 can be greater than 50 nm in length. The size of the nanopores are sometimes classified as micropores, which have at least two dimensions that do not exceed about 2 nm, and mesopores, which have at least two dimensions that range from about 2 to 50 nm. Both micropores and mesopores are referred to herein as nanopores. Pores with at least two dimensions greater than about 50 nm are referred to herein as macropores, and a macroporous material is a material that contains macropores. It should be noted, however, that nanoporous coatings and materials may further comprise macropores, provided that they also contain micropores and/or mesopores.

Depending on the pore size, it is known that nanoporous regions having parallel or near parallel pore structures can release species such as therapeutic agents in accordance with zero order kinetics. In other less-structured release-controlling regions, the species may travel through the region via interconnected networks of pores. In some instances, the lateral dimensions (e.g., the radii) of the interconnected pores approach the lateral dimensions (e.g., the hydrated radius) of the species that is being transported. Consequently, the species may move within, and ultimately be released from, pores of these diameters (as opposed to being trapped by pores having smaller radii). Under such circumstances, the interactions between the species and the walls of the nanopores will have a significant effect upon the transport that is observed. Indeed, as the diameter of the pore approaches the diameter of the species that is being transported, the surface interactions begin to dominate transport. See, e.g., Tej al A. Desai, Derek Hansford and Mauro Ferrari, "Characterization of micromachined silicon membranes for immunoisolation and bioseparation applications" J. Membrane Science, 159 (1999) 221-231, which describes insulin release through silicone nanomembranes. As with parallel pore structures, the interconnected pore structures are capable of transporting species in a highly controlled manner, and they have the potential to approach zero order transport kinetics where pore diameters approach the size of the species that is being transported. The transport rate may also be affected by the depth and tortuousity of the pores within the interconnected porous network. Furthermore, nanoporous regions in which pores form an interconnected network may allow species to diffuse laterally, for example, allowing a therapeutic agent to be released laterally beyond the boundaries of an underlying therapeutic-agent-containing region. Pores that are positioned too far laterally from the therapeutic-agent-containing region to participate in species transport may, nonetheless, promote cell adhesion. See, e.g., E. E. L. Swan, K. C. Popat, C. A. Grimes, T. A. Desai, "Fabrication and evaluation of nanoporous alumina membranes for osteoblast culture," *Journal of Biomedical Materials Research Part A*, Volume 72A, Issue 3, Pages 288-295, Published Online: 14 Jan. 2005, which describes osteoblast response to surface topography in anodized nanoporous alumina membranes.

In some cases the nanoporous region 140 may be prefabricated as a membrane that is subsequently placed over the therapeutic agent-containable region 115 and secured to the region 115 and/or the substrate 110 by any appropriate means. In other cases the nanoporous regions may be formed directly on the medical device.

Polymeric nanoporous membranes can be formed from a wide variety of polymers, including polycarbonate, cellulose acetate, and nylon. Specific examples of such polymers that may be used to form nanoporous membranes include cellulose acetates, cellulose nitrate, regenerated cellulose, perfluorosulfonic acid polymer, polyacrylonitrile, polyetherimides, polyethersulfones, polyethylene terephthalate, polyphenylene oxide, sulfonated or aminated poly(styrene-co-divinylbenzene), polytetrafluoroethylene, polyamide, aromatic polycarbonate, polyether, polyethylene, polyimide, polypropylene, polysiloxanes, polysulfones, polyvinyl alcohol and polyvinylidenefluoride. These and additional polymeric membranes are discussed in M. Ulbricht, "Advanced Functional Polymer Membranes," Polymer 47 (2006) 2217-2262, which is hereby incorporated by reference in its entirety. In some cases nanoporous membranes suitable for use in the present invention may be commercially available. For example, polycarbonate nanofilters with pore sizes down to 10 nm are currently available from the Sterlitech Corp. in Kent Wash.

When a prefabricated membrane is employed, the therapeutic agent may be first applied to either the substrate 110 or the membrane itself. The therapeutic agent may be applied to the bottom surface of the membrane (i.e., the surface of the membrane that will directly face the substrate 110) as a film that is coated or otherwise deposited onto the membrane using any of a number of processes, including, for example, spraying, coating with an applicator (e.g., by roller or brush), spin-coating, web coating, techniques involving coating via mechanical suspension including air suspension, and ink jet techniques, and combinations of these processes, among other techniques.

Regardless of whether therapeutic agent is first applied to the substrate or the nanoporous membrane, the nanoporous membrane may be secured in place over the substrate using a laser or other point heat source to melt the membrane along its perimeter.

Various examples of techniques which may be employed for forming nanoporous regions or layers are summarized below. Using such techniques, the nanoporous region may be formed on, or formed and then attached to, a wide range of substrates.

In some embodiments, a precursor region is formed, which is subsequently converted into a nanoporous region. For example, a mask with nano-scale apertures may be formed on a precursor region using known lithographic techniques, including optical, ultraviolet, deep ultraviolet, electron beam, and x-ray lithography, and subjected to further processing. For instance, a process for forming nanoporous silicon is described in L. Leoni, D. Attiah and T. A. Desai, "Nanoporous Platforms for Cellular Sensing and Delivery," *Sensors* 2002, 2, 111-120.

In some embodiments, a precursor region is formed which comprises first and second materials. Subsequently, the precursor region is subjected to conditions where the first material is either reduced in volume or eliminated from the precursor region. By providing nanodomains of the first material within the precursor region, a nanoporous region may be formed. Materials for forming such removable or size-reducible nanodomains include (a) materials that are converted into gaseous species upon heating, for example, materials that sublime, materials that melt and then evaporate, and materials that form gaseous reaction products such as combustible materials, (b) metal oxides which may be reduced to their corresponding metal, resulting in a loss in volume, (c) materials which are dissolved or otherwise removed in a solution, and so forth.

Some of these techniques rely on the ability of certain materials to phase separate into nanodomains. For example, nanoporous regions may be produced from a metal alloy that contains two or more metals of differing nobility and at least one of the less noble metals is oxidized and remove from the alloy, thereby forming a nanoporous region. In these embodiments, the at least one less noble metal corresponds to the nanodomains described above. Various methods are available for oxidizing and removing the less noble metal(s) from the metal mixture, including (i) contact with an appropriate acid (e.g., nitric acid), (ii) application of a voltage of sufficient magnitude and bias during immersion in a suitable electrolyte, and (iii) heating in the presence of oxygen, followed by dissolution of the resultant oxide. Examples include alloys of essentially any substantially non-oxidizing noble metal (e.g., gold, platinum, etc.) having nanodomains of essentially any metal that can be removed (e.g. Zn, Fe, Cu, Ag, etc.). Specific examples of suitable alloys include alloys comprising gold and silver (in which the silver is oxidized and removed), alloys comprising gold and copper (in which the copper is oxidized and removed), and so forth. Further details concerning de-alloying can be found, for example, in J. Erlebacher et al., "Evolution of nanoporosity in de-alloying," *Nature*, Vo. 410, 22 Mar. 2001, 450-453; A. J. Forty, "Corrosion micromorphology of noble metal alloys and depletion gilding," *Nature*, Vol. 282, 6 Dec. 1979, 597-598; R. C. Newman et al., "Alloy Corrosion," *MRS Bulletin*, July 1999, 24-28; and U.S. patent Appln. Pub. No. 2004/0148015 assigned to Setagon.

High-density arrays of nanopores with high aspect ratios may also be formed based on the self-assembly of incompatible nanodomains using block copolymers. Cylindrical nanopores may be formed, for example, using diblock copolymers composed of polymethylmethacrylate (PMMA) and polystyrene (PS). The molecular weight and volume fraction of styrene may be selected such that the copolymer self-assembles into arrays of PMMA cylinders hexagonally packed in a PS matrix. The PMMA cylinders may be oriented parallel to each other by applying an electric field, while the copolymer film is heated above the glass transition temperature. Deep ultraviolet exposure may be used to degrade the PMMA domains and simultaneously crosslink the PS matrix. The PMMA domains may be selectively removed by rinsing the film with acetic acid, yielding a PS film with ordered nanopores. For further information, see, e.g., H. X. He and N. J. Tao, "Electrochemical fabrication of metal nanowires" in Encyclopedia of Nanoscience and Nanotechnology, Eds., N. S. Nalwa, American Scientific Publishers, 2003, and the references cited therein.

In some embodiments, nanoporous regions are formed using physical vapor deposition (PVD) techniques. For example, films grown by PVD techniques at lower temperatures (e.g., where the ratio of the temperature of the substrate, $T_s$, relative to the melting point of the deposited of the film, $T_m$, is less than 0.3) have been observed to produce films that tend to be more porous than films produced at higher temperatures.

PVD techniques can also be used to deposit two or more materials, followed by removal of one or more of the materials to produce a nanoporous region. For example, two or more metals may be simultaneously deposited via PVD (e.g., by sputtering separate targets of a single metal or by sputtering a single target containing multiple metals), followed by annealing if necessary to cause phase separation, which is followed by de-alloying, for example, using techniques such as those described above.

Some embodiments of the invention employ chemical vapor deposition (CVD) techniques, including low-pressure chemical vapor deposition (LPCVD) processes and plasma-enhanced chemical vapor deposition (PECVD) processes, in the formation of nanoporous regions. For example, it is known to deposit nanoporous silicon dielectric films (e.g., silicon oxide films such as silicon dioxide) by PECVD using organosilicate precursor compounds such as tetraethylorthosilicate (TEOS), typically in the presence of an oxidant such as $N_2O$, $O_2$, $O_3$, $H_2O_2$, etc. See e.g., United States Patent Application No. 2002/0142579 to Vincent et al.

As another example, it is known to deposit nanoporous silicon oxycarbide films (specifically SiOCH, also known as hydrogenated silicon oxycarbide) by PECVD oxidation of $(CH_3)_3SiH$ in the presence of an oxidant (i.e., $N_2O$). See, e.g., D. Shamiryan et al., "Comparative study of SiOCH low-k films with varied porosity interacting with etching and cleaning plasma," *J. Vac. Sci. Technol. B*, 20(5), September/October 2002, pp. 1923-1928.

As another example, in a process known as particle-precipitation-aided chemical vapor deposition (PP-CVD), an aerosol of particles is first formed by a gas phase reaction at elevated temperature. The particles are then deposited on a substrate, for example, due to the forces of electrophoresis, thermophoresis, or forced flow. In certain embodiments, a heterogeneous reaction occurs simultaneously with deposition to interconnect the particles and form a nanoporous layer, or the deposited particles are sintered to form a nanoporous layer, or both. As a specific example, a $CO_2$ laser may be used to heat metallorganic precursor compounds in the gas phase, resulting in decomposition of the precursor with concomitant formation of an aerosol of ceramic nanodomains. The particles are then deposited on a substrate as a result of a thermal gradient that naturally exists between the heated reaction zone created by the laser and the cooler substrate. In this example, heterogeneous reactions at the substrate surface can be controlled independently of the gas phase reactions. Further information can be found in *Handbook of Nanophase and Nanostructured Materials*. Vol. 1. Synthesis. Zhong Lin Wang, Yi Liu, and Ze Zhang, Editors; Kluwer Academic/Plenum Publishers, Chapter 5, "Chemical Vapor Deposition".

As another example, in hot-filament CVD (HFCVD), also known as pyrolytic or hot-wire CVD, a precursor gas is thermally decomposed by a resistively heated filament. The resulting pyrolysis products then adsorb onto a substrate maintained at a lower temperature (typically around room temperature) and react to form a film. One advantage associated with pyrolytic CVD is that the underlying substrate can be maintained at or near room temperature. As a result, films can be deposited over underlying regions that comprise a wide range of therapeutic agents, including many therapeutic agents that cannot survive other higher-temperature processes due to their thermal sensitivities. For example, in some embodiments, a fluorocarbon polymer film is prepared by exposing a fluorocarbon monomer (e.g., hexafluoropropylene oxide, among others) to a source of heat having a temperature sufficient to pyrolyze the monomer and produce a reactive species that promotes polymerization. By maintaining the substrate region in the vicinity of the reactive species and maintaining the substrate region at a substantially lower temperature than that of the heat source, deposition and polymerization of the reactive species on the structure surface are induced. In other embodiments, fluorocarbon-organosilicon copolymer films are prepared by exposing a fluorocarbon monomer (e.g., hexafluoropropylene oxide, among others) and an organosilicon monomer (e.g., hexamethylcyclotrisiloxane or octamethylcyclotetrasiloxane, among others) to the heat source. Due to the nucleation and growth mechanisms in the HFCVD processes, nanoporous films can be made using HFCVD. For further information, see, e.g., United States Patent Application No. 2003/0138645 to Gleason et al., U.S. Pat. No. 6,156,435 to Gleason et al., and K. K. S. Lau et al., "Hot-wire chemical vapor deposition (HWCVD) of fluorocarbon and organosilicon thin films," *Thin Solid Films*, 395 (2001) pp. 288-291, each of which is incorporated by reference in its entirety.

In some cases, multiple deposition techniques are combined to form nanostructured regions on medical devices. One specific example is the deposition of polymers (e.g., by plasma enhanced polymerization) concurrently with PVD-type deposition of metals to produce mixed metal-polymer films. See "Plasma Polymer-Metal Composite Films,: H. Biedermann and L. Nartinu, p. 269 in *Plasma Deposition, Treatment and Etching of Polymers*, Riccardo d'Agostino, Ed., Academic Press (1990). Nanoporous regions may be formed by selectively removing the polymer or the metal phase from the mixed film.

In still other embodiments of the present invention, nanoporous regions are formed by processes that comprise a technique commonly referred to as "kinetic metallization." In the kinetic metallization technique, metal particles (e.g., metal nanoparticles) are impacted with a substrate at high speed (e.g., at supersonic or near supersonic velocities) and at a temperature that is well below the melting point(s) of the metal particles (e.g., at a low temperature, such as ambient temperature). In certain embodiments, the metal particles are mixed with a relatively inert gas such as helium and/or nitrogen in a powder fluidizing unit, and the resulting fluidized powder is sprayed at high velocity onto the substrate. When the particles strike the substrate, fresh active metal is exposed, leading to adhesive and cohesive metallurgical bonding of the metal particles with the substrate and with one another. Because the particles are deposited at well below their respective melting points, the particles remain solid. Hence, like many of the above deposition techniques, they can form mixtures of metals that may be immiscible as liquids. Moreover, heat distortion of the substrate and interdiffusion of multilayer coatings can be minimized or avoided. Additional information on this process can be found, for example, in U.S. Pat. Nos. 5,795,626 and 6,074,135, U.S. Patent Application Nos. 2002/0168466 A1 and 2003/0006250 A1, and International Publication Number WO 02/085532 A1, all to Howard Gabel and Ralph Tapphorn.

The metal particles in this technique may be, for example, particles of metal alloy, a mixture of pure metal particles, a mixture alloy particles, and so forth. Examples of particles for use in these methods include particles of the various metals described herein, including particles of gold, platinum, aluminum, cobalt, titanium, niobium, zinc, iron, copper, silver, tungsten, nickel, chromium, as well as alloys based on these and other metals. These and other particles can be used coat metal substrates (e.g., aluminum, titanium, stainless steel and nitinol substrates), as well as semiconductor, ceramic and polymer substrates, for example, those formed from the various substrate materials described herein. Once a nanostructured surface containing a mixture of metal nanoparticles is formed, one metal may be preferentially removed using techniques such as those discussed above (e.g., de-alloying), thereby producing a nanoporous region.

In some embodiments, nanoporous regions are formed using electrochemical methods. For example, materials with nanodomains may be formed by first incorporating suspended nanoparticles into a matrix that is formed by electrodeposition and/or electroless deposition. (For example, nanoparticles that are dispersed by adsorbing cations on their surfaces, are known to travel to the cathode where electrodeposition takes place, such that the nanoparticles are incorporated into the deposited layer.). Once formed, such nanodomains are subsequently reduced in size as discuss above (e.g., by sublimation, evaporation, combustion, dissolution, etc.).

Another example of an electrochemical technique is the anodization of aluminum to form nanoporous alumina. The individual nanopores that are formed in the alumina upon anodization may be ordered into a hexagonally packed structure, with the diameter of each pore and the separation between two adjacent pores being controlled by changing the anodization conditions. Pore ordering has been shown to be improved using high-purity aluminum films, which are preannealed and electropolished Pore ordering also depends on anodization conditions, such as anodization voltage and the electrolyte. Pore ordering may be promoted through the use of a pre-texturing process in which an array of shallow concave features is initially formed on aluminum by indentation. Pore ordering may also be promoted by employing a two-step anodization method. The first step involves anodization of high purity aluminum to form a porous alumina layer. This layer is then dissolved, yielding a patterned aluminum substrate with an ordered array of concave features formed during the first anodization step. The ordered concave features then serve as the initial sites to form a highly ordered nanopore array in a second anodization step. Aluminum anodization normally results in a porous alumina structure which is separated from the aluminum substrate by a layer of $Al_2O_3$. The $Al_2O_3$ layer and aluminum substrate may then be removed to form a free-standing porous alumina membrane. For further information, see, e.g., H. X. He and N. J. Tao, "Electrochemical fabrication of metal nanowires" in Encyclopedia of Nanoscience and Nanotechnology, Eds., N. S. Nalwa, American Scientific Publishers, 2003, and the references cited therein. See also E. E. L. Swan, K. C. Popat, C. A. Grimes, T. A. Desai, "Fabrication and evaluation of nanoporous alumina membranes for osteoblast culture," Journal of Biomedical Materials Research Part A, Volume 72A, Issue 3, Pages 288-295, Published Online: 14 Jan. 2005, which describes osteoblast response to surface topography in anodized nanoporous alumina membranes. Alumina membranes with pore sizes ranging from 30 to 80 nm are reported.

In some embodiments of the invention, nanoporous regions are formed using sol-gel techniques. The starting materials that are used in the preparation of sol-gel regions are frequently inorganic metal salts, metallic complexes (e.g., metal acetylacetonate complexes), or organometallic compounds (e.g., metal alkoxides). Typically, the starting material is subjected to hydrolysis and polymerization (sometimes referred to as a condensation) reactions to form a colloidal suspension, or "sol". Further processing of the sol enables ceramic materials to be made in a variety of different forms. For instance, thin films can be produced on a substrate, for example, by spray coating, coating with an applicator (e.g., by roller or brush), spin-coating, or dip-coating of the sol onto the substrate, whereby a wet gel is formed. Where dip coating is employed, the rate of withdrawal from the sol can be varied to influence the properties of the film. The wet gel is then dried. The porosity of the gel can be regulated in a number of ways, including, for example, varying the solvent/water content, varying the aging time, varying the drying method and rate, and so forth. In certain embodiments, sol-gel processing is carried out at low temperatures (e.g., temperatures of 15-35° C.). In other embodiments, the sol-gel is subjected to high temperatures, for example, temperatures of 100° C., 200° C., 300° C., 400° C., 500° C., or more. Such high temperatures commonly reduce the porosity of the sol-gel, while at the same time increasing its mechanical strength. Where the biologically active agent is present at high temperatures, care should be taken to avoid thermal damage to the same. Further information concerning sol-gel materials can be found, for example, in Viitala R. et al., "Surface properties of in vitro bioactive and non-bioactive sol-gel derived materials," Biomaterials. 2002 August; 23 (15):3073-86; Radin, S. et al., "In vitro bioactivity and degradation behavior of silica xerogels intended as controlled release materials," Biomaterials. 2002 August; 23 (15):3113-22; Nicoll S. B., et al., "In vitro release kinetics of biologically active transforming growth factor-beta 1 from a novel porous glass carrier," Biomaterials. 1997 June; 18 (12):853-9; Santos, E. M. et al., "Sol-gel derived carrier for the controlled release of proteins," Biomaterials. 1999 September; 20 (18):1695-700; Radin, S. et al., "Silica sol-gel for the controlled release of antibiotics. I. Synthesis, characterization, and in vitro release," J Biomed Mater Res. 2001 November; 57 (2):313-20; Aughenbaugh, W. et al., "Silica sol-gel for the controlled release of antibiotics. II. The effect of synthesis parameters on the in vitro release kinetics of vancomycin," J Biomed Mater Res. 2001 Dec. 5; 57 (3):321-6; Santos, E. M. et al., "Si—Ca—P xerogels and bone morphogenetic protein act synergistically on rat stromal marrow cell differentiation in vitro," J Biomed Mater Res. 1998 July; 41 (1):87-94.

High porosity, uniform-pore-size mesoporous silicon oxide and aluminum oxide films may also be prepared by sol-gel methods using block copolymers as the structure-directing agents. For example, J.-A. Paik et al. "Micromachining of mesoporous oxide films for microelectromechanical system structures," J. Mater. Res., Vol. 17, No. 8, August 2002, 2121 has reported the formation of films that are over 50% porous with uniform pores of 8-nm average diameter.

Further information on nanoporous regions and methods for making them can be found, for example, in U.S. patent Ser. No. 11/007,867 entitled "Medical Devices Having Nanostructured Regions For Controlled Tissue Biocompatibility And Drug Delivery" and U.S. patent Ser. No. 11/007,877 entitled "Medical Devices Having Vapor Deposited Nanoporous Coatings For Controlled Therapeutic Agent Delivery," each filed 9 Dec. 2004 and each of which is hereby incorporated by reference in its entirety.

As previously mentioned, a macroporous non-polymeric region or layer (e.g., macroporous non-polymeric layer 150 in FIG. 1) is disposed over the nanoporous polymeric layer to isolate the polymeric material from surrounding tissue during in-situ delivery of the therapeutic agents. The macroporous non-polymeric region or layer may be formed on, or formed and then attached to, the nanoporous polymeric layer. The macroporous non-polymeric region or layer may be formed, for example, from any suitable inorganic material including metallic materials (e.g., metals and metal alloys) and non-metallic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others). Some specific examples of metallic and non-metallic inorganic materials have been mentioned above in connection substrate 110 in FIG. 1.

In some embodiments of the invention the macroporous non-polymeric region or layer may be formed directly on the nanoporous polymeric layer using a deposition technique such as sputtering, for example. One example of a sputtering technique that may be particularly suitable for the deposition of the macroporous non-polymeric region or layer involves use of the nanocluster deposition system available from Mantis Ltd. The Mantis system employs a high pressure magnetron sputtering source to generate nanoparticles within a condensation zone. The magnetron has a negative bias and a large fraction (e.g., about 40%) of the nanoparticles have a charge of one electron. The ionized nanoparticles emerge from the source with a low kinetic energy to ensure that the particles retain their structure when they are subsequently deposited on the nanoporous polymer layer 140. A filter may be employed so that only larger particles (e.g., greater than 10 nm) are deposited. For example, a linear quadrapole device may be placed after the exit aperture of the magnetron chamber to select nanoparticles within the desired size range.

Spray deposition is another example of a technique that may be used to form the macroporous non-polymeric region. Spray deposition involves the deposition of a powder suspension onto a heated substrate followed by room temperature compression. The use of spray deposition to form $TiO_2$ nanoparticle films for use in solar cells is discussed in Janne Halme, "Spray Deposition and Compression of $TiO_2$ Nanoparticle Films for Dye-Sensitized Solar Cells on Plastic Substrates," Solar Energy Materials & Solar Cells 90 (2006) 887-899.

Figure 2:
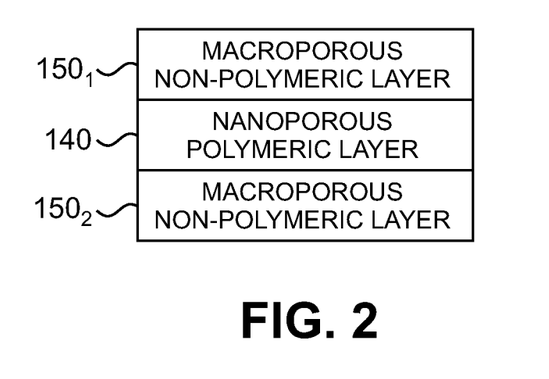
FIG. 2 shows a schematic cross-section through a tri-layer membrane that includes a centermost nanoporous polymer layer covered on both sides by macroporous non-polymeric regions, which membrane may be employed in various embodiments of the invention.

When the nanoporous polymeric layer is a prefabricated membrane, the macroporous non-polymeric region may be formed (e.g., by deposition) on the nanoporous polymeric membrane either before or after the membrane is secured over the substrate. That is, when the membrane is secured to the substrate, it may be configured as a bi-layer membrane that includes the nanoporous polymeric layer 140 and the macroporous non-polymeric region 150 (see FIG. 1) or even as a tri-layer that includes therapeutic agent layer 115, the nanoporous polymeric layer 140 and the macroporous non-polymeric region 150. In some cases the membrane may include additional layers as appropriate. For example, as shown in FIG. 2, a tri-layer membrane (not including a therapeutic agent layer) may include a centermost nanoporous polymer layer 140 that is covered on both sides by macroporous non-polymeric regions 150$_1$ and 150$_2$.

Figure 3:
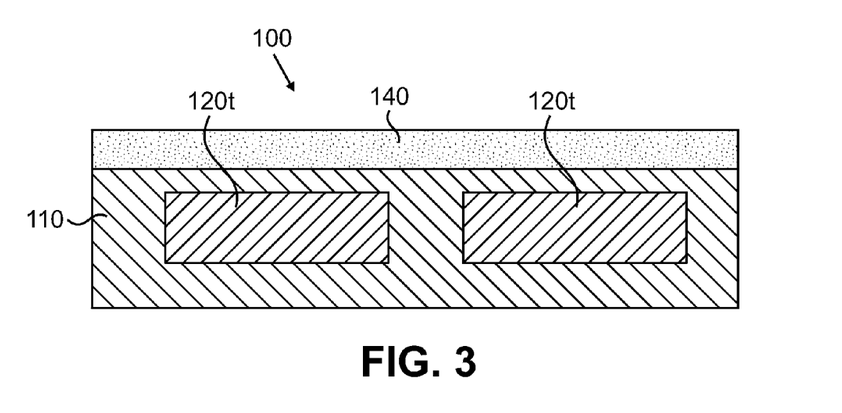
FIG. 3 is a schematic cross-sectional view of two drug-filled depressions that are capped with a nanoporous region, in accordance with an embodiment of the invention.

In some embodiments of the invention the therapeutic agent-containable region may be provide in the form of depressions that are formed in the substrate. By way of example, FIG. 3 is a schematic cross-section illustrating two therapeutic-agent-containing depressions 120*t* within a portion 110 of a medical device 100 such as those described above. The therapeutic-agent-containing depressions are capped by the nanoporous polymeric layer 140 and the macroporous non-polymeric layer 150.

Multiple (e.g., 2 to 5 to 10 to 25 to 50 to 100 or more) or single therapeutic agent filled depressions 120*t* and/or multiple or single nanoporous coatings 140 may be provided, if desired. Therapeutic-agent-containing depression(s) 120*t* with associated porous region(s) 140 may be provided over the entire device or only over one or more distinct portions of the device. For example, for tubular devices such as stents (which can comprise, for example, a laser or mechanically cut tube, among other designs), therapeutic-agent-filled depression(s) 120*t* with associated porous region(s) 140 may be provided on the luminal device surfaces, on the abluminal device surfaces, and/or on the lateral device surfaces between the luminal and abluminal surfaces. It is therefore possible, for example, to provide different therapeutic agents at different locations on the medical device. For example, it is possible to provide one or more first depressions filled with a first therapeutic agent (e.g., an antithrombotic agent) at the inner, luminal surface of the device, and one or more second depressions filled with a second therapeutic agent that differs from the first therapeutic agent (e.g., an antiproliferative agent) at the outer, abluminal surface. One may also provide more than one therapeutic agent in separate depressions on the luminal surface or the abluminal surface.

Figure 4A:
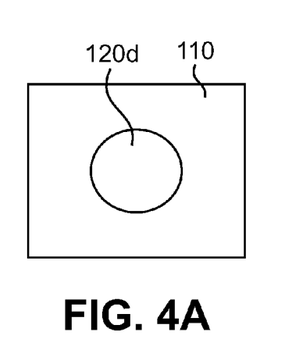
FIGS. 4A-4G and 5A-5E are schematic top views illustrating various depression configurations and arrays of the same, in accordance with various embodiments of the invention.
Figure 4B:
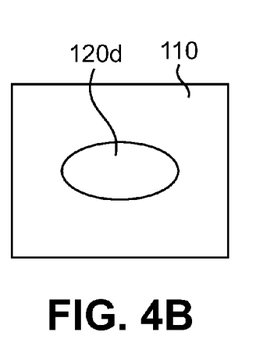
Figure 4C:
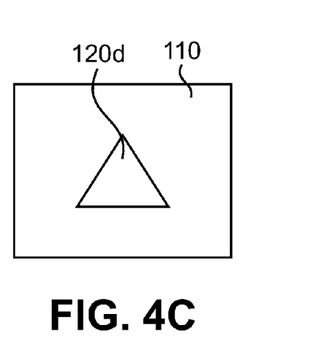
Figure 4D:
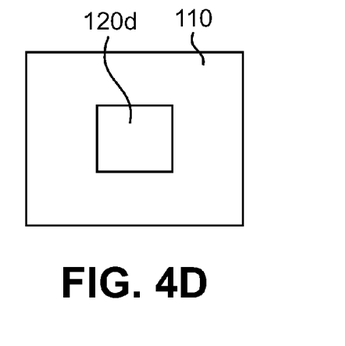
Figure 4E:
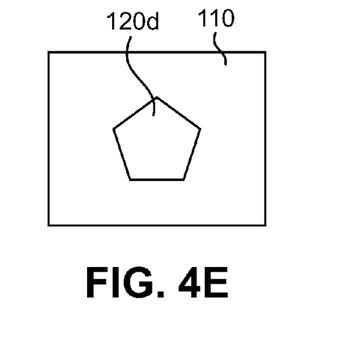
Figure 4F:
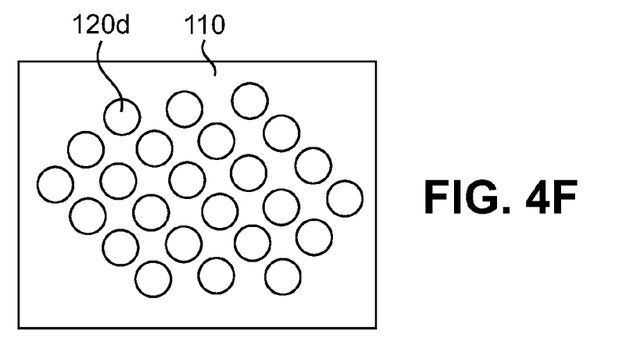
Figure 4G:
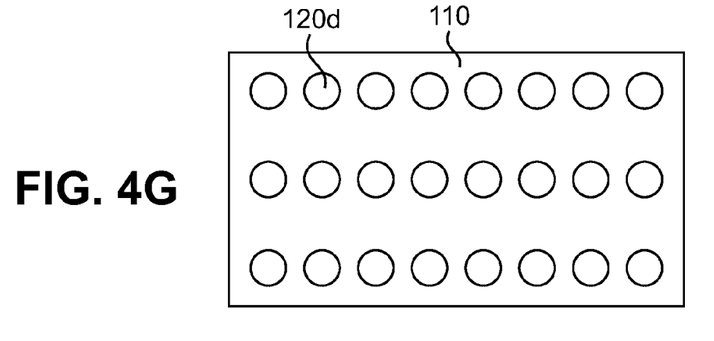
Figure 5A:
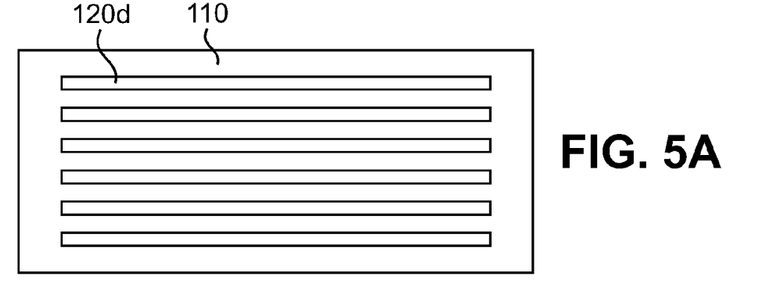
Figure 5B:
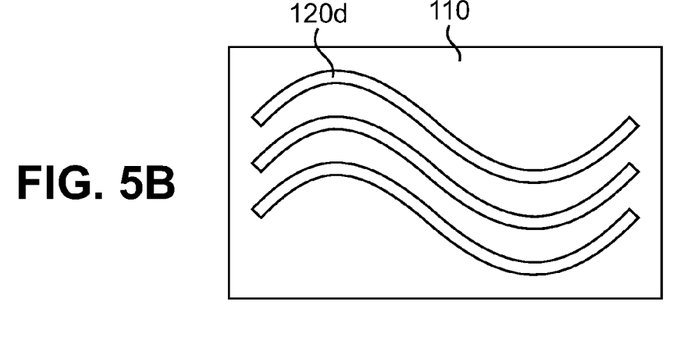
Figure 5C:
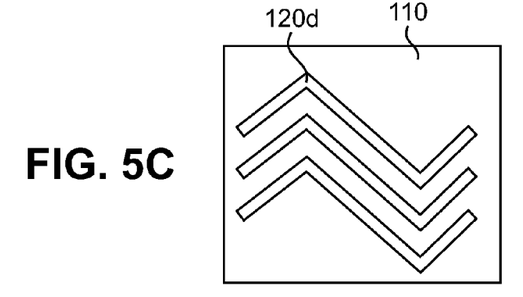
Figure 5D:
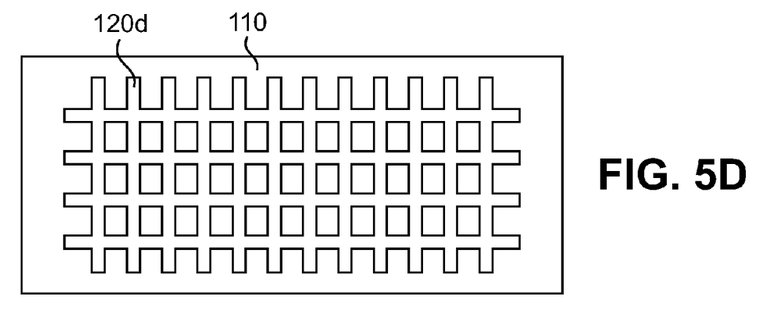
Figure 5E:
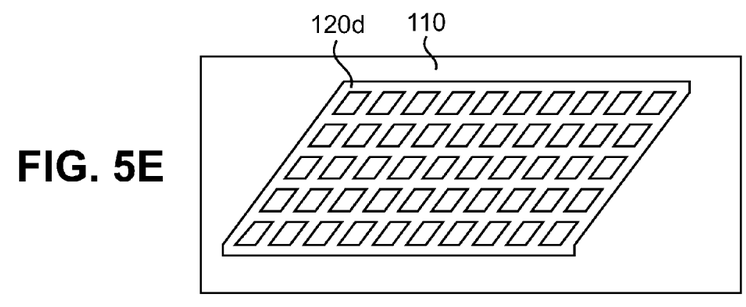

The depressions which contain the therapeutic agents may come in various shapes and sizes and can extend partially or completely through the substrate. Examples include depressions whose lateral dimensions are circular (see, e.g., the circular hole of FIG. 4A, in which the depressed area 120*d* within the medical device portion 110 is designated with a darker shade of grey), oval (see FIG. 4B), polygonal, for instance triangular (see FIG. 4C), rectangular (see FIG. 4D), pentagonal (see FIG. 4E), as well as holes of various other regular and irregular shapes and sizes. Multiple holes 120*d* can be provided in a near infinite variety of arrays. See, e.g., FIGS. 4F and 4G (one hole numbered in each). Further examples include trenches, such as simple linear trenches (see FIG. 5A, one trench numbered), wavy trenches (see FIG. 5B, one trench numbered), trenches formed from linear segments whose direction undergoes an angular change (see FIG. 5C, one trench numbered), trenches intersecting at right angles (see FIG. 5D) as well as other angles (see FIG. 5E), as well as other regular and irregular trench configurations.

In general, the medical devices of the invention contain depressions whose smallest lateral dimension (e.g., the diameter for a cylindrical depression, the width for an elongated depression such a trench, etc.) is less than 1 mm (1000 µm), for example, ranging from 1000 µm to 500 µm to 250 µm to 100 µm to 50 µm to 10 µm to 5 µm to 2.5 µm to 1 µm or less. The pores of the nanoporous transport-controlling regions generally will be substantially smaller than the smallest lateral dimensions of the depressions over which they are positioned.

Figure 6A:
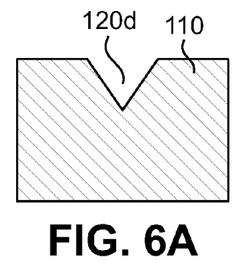
FIGS. 6A-6E and 7A-7D are schematic cross-sectional views illustrating various depression configurations, in accordance with various embodiments of the invention.
Figure 6B:
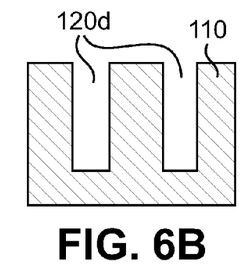
Figure 6C:
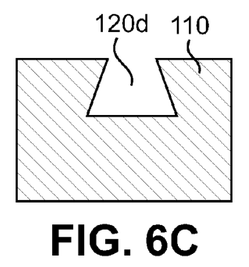
Figure 6D:
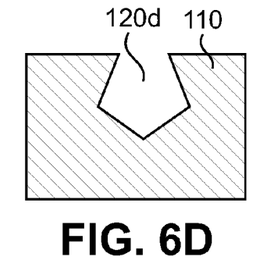
Figure 6E:
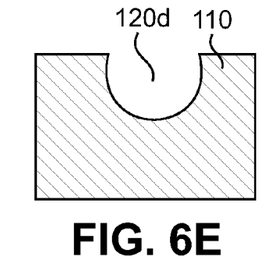
Figure 7A:
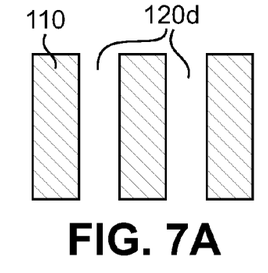
Figure 7B:
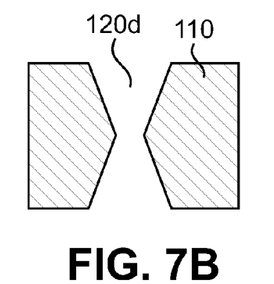
Figure 7C:
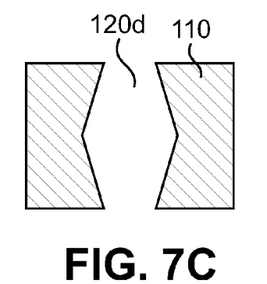
Figure 7D:
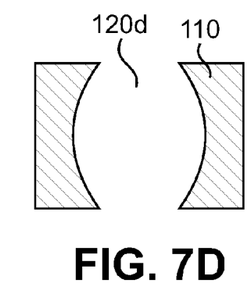

In some embodiments, the depressions 120*d* extend only partially into the medical device portion 110, for example, being in the form of blind holes, trenches, etc. Such depressions may have a variety of cross-sections, such as polygonal cross-sections, including triangular (see, e.g., FIG. 6A), quadrilateral (see, e.g., FIGS. 6B and 6C) and pentalateral (see, e.g., FIG. 6D) cross-sections, and semicircular cross-sections (see, e.g., FIG. 6E), as well as other regular and irregular cross-sections. In certain embodiments, the depressions are high aspect ratio depressions, meaning that the depth of the depression is greater than or equal to the smallest lateral dimension of the depression, for example, ranging from 1 to 1.5 to 2 to 2.5 to 5 to 10 to 25 or more times the smallest lateral dimension (e.g., the depth for a cylindrical depression is greater than or equal to its diameter, the depth for an elongated depression such as a trench is greater than or equal to its width, etc.). FIG. 6B illustrates two high aspect depressions 120*d* in cross-section. In some embodiments the depressions 120*d* may extend through the medical device portion 110, for example, bein7 in the form of through-holes, slots, etc. See, e.g., the cross-sections of FIGS. 7A-7D.

Examples of techniques for forming depressions (e.g., blind holes, through holes, slots, trenches, etc.) for use in the invention include molding techniques, direct-write techniques, and mask-based techniques, in which masking is used to protect material that is not to be removed.

In molding techniques, a mold may be provided with various protrusions, which after casting the medical article of interest, create depressions for use in the invention.

Direct write techniques include those in which depressions are created through contact with solid tools (e.g., microdrilling, micromachining, etc., using high precision equipment such as high precision milling machines and lathes) and those that form depressions without the need for solid tools (e.g., those based on directed energetic beams such as laser, electron, and ion beams). In the latter cases, techniques based on diffractive optical elements (DOEs), holographic diffraction, and/or polarization trepanning, among other beam manipulation methods, may be employed to generate direct-write patterns as desired. Using these and other techniques multiple voids can be ablated in a material layer at once.

Mask-based techniques include those in which the masking material contacts the layer to be machined (e.g., where masks that are formed using known lithographic techniques, including optical, ultraviolet, deep ultraviolet, electron beam, and x-ray lithography) and techniques in which the masking material does not contact the layer to be machined, but which is provided between a directed source of excavating energy and the material to be machined (e.g., opaque masks having apertures formed therein, as well as semi-transparent masks such as gray-scale masks which provide variable beam intensity and thus variable machining rates). One process, known as columnated plasma lithography, is capable of producing X-rays for lithography having wavelengths on the order of 10 nm. Material is removed in regions not protected by the above masks using any of a range of processes including physical processes (e.g., thermal sublimation and/or vaporization of the material that is removed), chemical processes (e.g., chemical breakdown and/or reaction of the material that is removed), or a combination of both. Specific examples of removal processes include wet and dry (plasma) etching techniques, and ablation techniques based on directed energetic beams such as electron, ion and laser beams.

In those embodiments of the invention where laser light is used for material removal, shorter wavelength light is often preferred. There are several reasons for this. For example, shorter wavelength light such as UV and deep-UV light can be imaged to a smaller spot size than light of longer wavelengths (e.g., because the minimum feature size is limited by diffraction, which increases with wavelength). Such shorter wavelength light is also typically relatively photolytic, displaying less thermal influence on surrounding material. Moreover, many materials have high absorption coefficients in the ultraviolet region. This means that the penetration depth is small, with each pulse removing only a thin layer of material, thereby allowing precise control of the drilling depth. Various lasers are available for laser ablation, including excimer lasers, solid state lasers such as those based on Nd:YAG and Nd:vanadate, among other crystals, metal vapor lasers, such as copper vapor lasers, and femtosecond lasers. Further information on lasers and laser ablation may be found in Lippert T, and Dickinson JT, "Chemical and spectroscopic aspects of polymer ablation: Special features and novel directions," *Chem. Rev.*, 103(2): 453-485 February 2003; Meijer J, et al., "Laser Machining by short and ultrashort pulses, state of the art and new opportunities in the age of photons," *Annals of the CIRP*, 51(2), 531-550, 2002, and U.S. Pat. No. 6,517,888 to Weber, each of which is hereby incorporated by reference.

It is noted that there is a great amount of available know-how in the semiconductor industry for etching holes (e.g., vias), trenches and other depressions in various materials. For this reason, in some embodiments of the invention, depressions for use in the present invention are formed in materials for which processing is routine in the semiconducting industry including semiconducting materials such as silicon, insulating materials such as silicon oxide, silicon nitride, and various metal oxides, and conductive materials, including a variety of metals and metal alloys. In certain embodiments, a layer of such a material is provided over another material that, for example, provides the device with desired mechanical characteristics. As one specific example, a silicon layer may be grown on a stainless steel or nitinol substrate and further processed to form depressions using known techniques.

The depressions within the substrates may or may not contain a therapeutic agent at the time the nanoporous region is introduced to the substrate. Some techniques for loading the depressions with the therapeutic agent will be presented below.

Figure 9A:
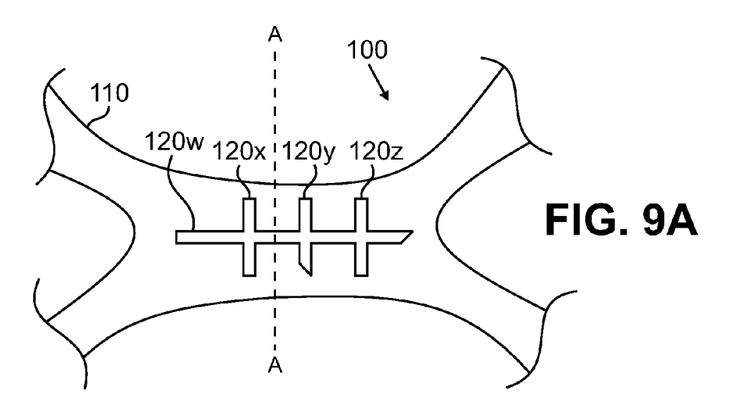
FIG. 9A is a schematic top view of a strut portion of a vascular stent, in accordance with an embodiment of the invention.
Figure 9B:
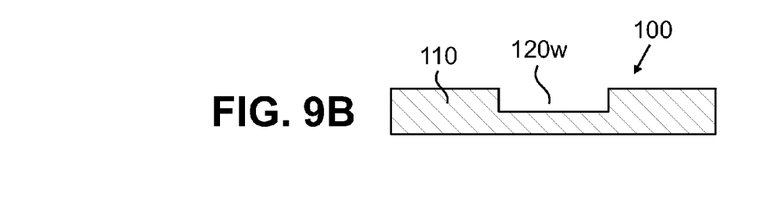
FIG. 9B is a schematic cross-sectional view of the strut portion of FIG. 9A, taken along line A-A.

With reference now to FIG. 9A a portion of a medical device is shown, specifically, a strut 110 of a stent 100, which may be formed from an organic or inorganic material (e.g., a metallic material such as stainless steel or nitinol, or a polymeric material such as a biodegradable polyester, among many other possibilities). Depressions, specifically an interconnecting network of trenches 120w, 120x, 120y, 120z, in the embodiment shown, are formed within the strut 110, which subsequently act as therapeutic agent reservoirs as discussed above. A cross section of the strut 110 and trench 120w is illustrated in FIG. 9B, which is taken along line A-A of FIG. 9A.

While the specific structure shown contains intersecting linear trenches having rectangular cross-sections, myriad other possibilities exist, as previously indicated, including the use of trenches that are non-linear, the use of non-intersecting trenches, the use of multiple holes instead of or in addition to trenches, the use of trenches and/or holes that have non-rectangular cross-sections, the use of trenches and/or holes that have high aspect ratio or extend through the strut, and so forth.

Figure 10:
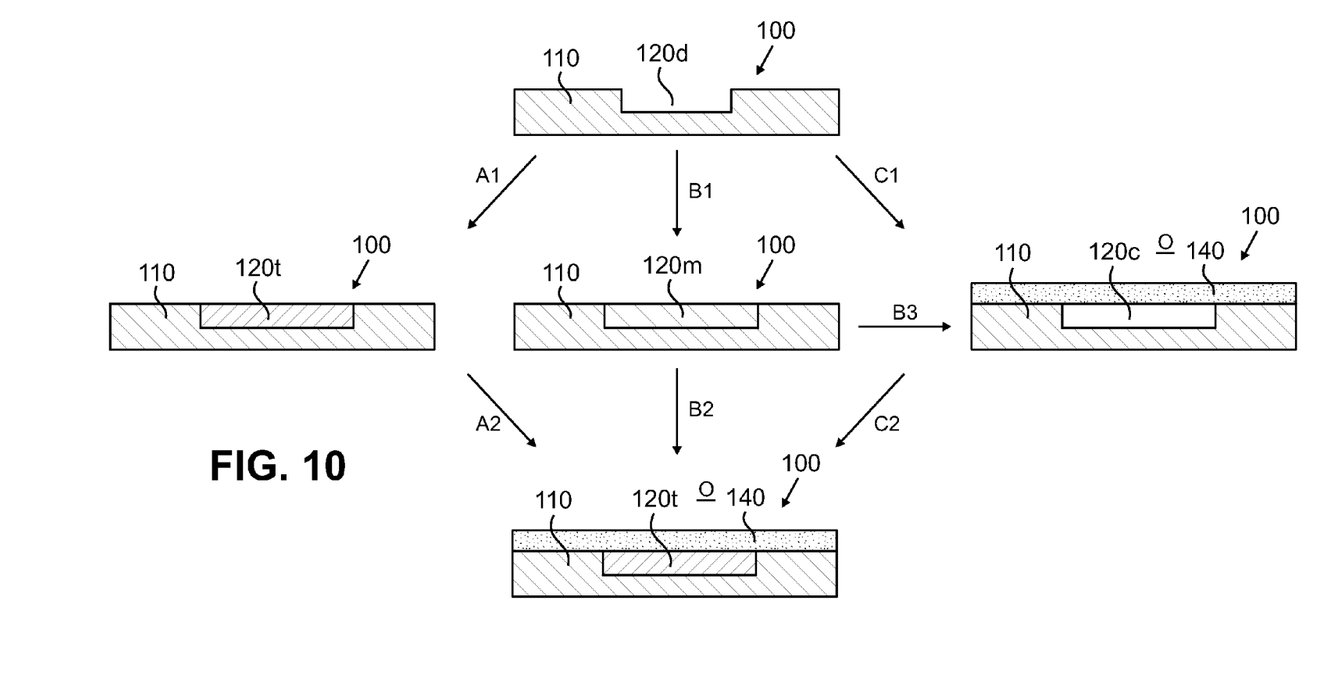
FIG. 10 is a schematic diagram illustrating examples of ways by which a depression within a medical device surface may be loaded with a therapeutic agent and provided with a nanoporous coating.

FIG. 10 schematically illustrates a few processes whereby a depression 120d within a medical device portion 110 may be loaded with a therapeutic agent 120t and whereby a nanoporous polymeric transport-controlling layer 140 and a macroporous non-polymeric layer 150 (not shown) may be established between the therapeutic agent 120t and outside environment O.

For example, in step A1 of FIG. 10, the depression 120d is first loaded with one or multiple therapeutic agents using any of a number of processes, including, for example, dipping, spraying, extrusion, coating with an applicator (e.g., by roller or brush), spin-coating, web coating, techniques involving coating via mechanical suspension including air suspension, ink jet techniques, and combinations of these processes, among other techniques. As noted above, the therapeutic agent(s) may be supplied in pure form or in combination with a supplemental material, such as a polymer matrix. The therapeutic agent(s) and any supplemental material may be supplied, for example, in particle form, in the form of a melt, in the form of a solution, etc.

A nanoporous polymeric transport-controlling layer 140 and a macroporous non-polymeric layer 150 are then provided over the therapeutic agent 120t as illustrated in step A2. As noted above, the nanoporous polymeric transport-controlling layer 140 and the macroporous non-polymeric layer 150 may be formed over the therapeutic agent 120t, or they may be first formed and then adhered over the therapeutic agent 120t.

In another variation, a nanoporous polymeric transport-controlling layer 140 and a macroporous non-polymeric layer 150 are first provided over the depression 120d, forming a cavity 120c as illustrated in step C1. The nanoporous polymeric transport-controlling layer 140 and the macroporous non-polymeric layer 150 may first be formed and then adhered over the depression 120d or they may be formed over the depression 120d. Once process step C1 is completed, the resulting cavity 120c is then loaded with a therapeutic agent 120t by conveying the therapeutic agent through the nanoporous region 140 and macroporous region 150, as illustrated in step C2. For example, a fluid containing dissolved or dispersed therapeutic agent (and suitable supplemental material(s), if desired) may be contacted with the porous regions 140 and 150, for instance, by dipping, spraying, extrusion, coating with an applicator (e.g., by roller or brush), spin-coating, web coating, techniques involving coating via mechanical suspension including air suspension, ink jet techniques, and combinations of these processes, among other techniques. Water, organic solvents, subcritical fluids, critical point fluids, supercritical fluids, and so forth can be used as carriers for the therapeutic agent. In one preferred technique, the solvent is a supercritical solvent. Further information on supercritical solvent loading may be found in U.S. Patent Publication No. US 2006-0127442 A1, filed 9 Dec. 2004 and entitled "Use of Supercritical Fluids to Incorporate Biologically Active Agents into Nanoporous Medical Articles."

In a further variation shown in FIG. 10, depression 120d is first filled with a material 120m that can subsequently uptake significant amounts of drug (e.g., a sponge-like material), as illustrated in step B1. Subsequently, as illustrated in step B2, the material 120m is loaded with a therapeutic agent 120t and a porous regions 140 and 150 are provided over the medical device portion 110 (or vice versa).

In yet another variation, in step B1 of FIG. 10, the depression 120d is filled with a removable material 120m. Then the nanoporous transport-controlling layer 140 and macroporous layer 150 are formed over the removable-material-filled depression 120m which removable material 120m is subsequently removed through the porous layers 140 and 150 producing a cavity 120c as illustrated in step B3. Removable material 120m may be removed by various processes, including melting, sublimation, combustion, dissolution, supercritical extraction, or other process. The cavity 120c is then loaded with a therapeutic agent 120t by conveying the therapeutic agent through the porous region 140, as illustrated in step C2 (discussed above).

Figure 11:
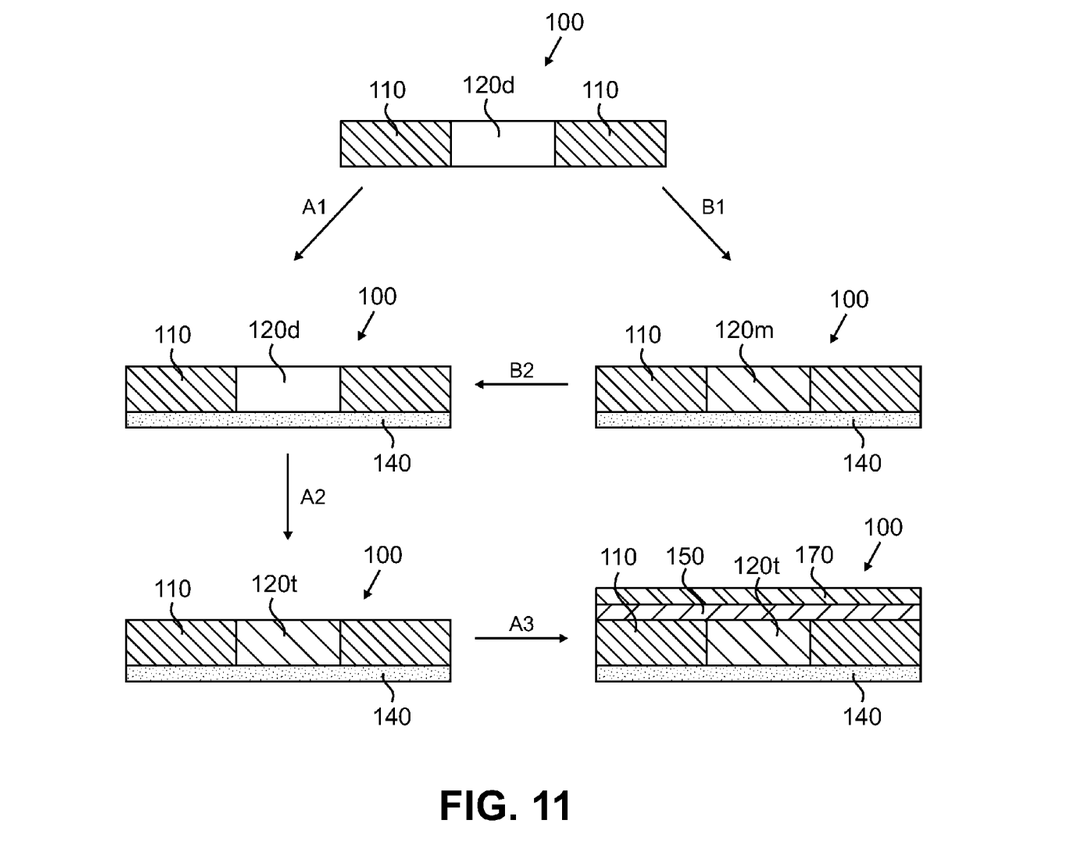
FIG. 11 is a schematic diagram illustrating examples of ways by which a depression within a medical device surface may be loaded with a therapeutic agent and provided with a nanoporous coating.

The use of depressions 120 that extend entirely through the device affords the opportunity to first form the nanoporous region 140 and macroporous region 150 over the depression, and then load the depression with therapeutic agent 120t, without having to pass the therapeutic agent through the nanoporous region 140 and the macroporous region 150. For example, with reference to FIG. 11, in which a depression 120d is shown that extends completely through the medical device portion 110, a nanoporous transport-controlling layer 140 and a macroporous layer 150 may be established over one surface of the device portion 110. This can be done directly as shown in step A1 (e.g., using techniques such as those described in conjunction with step C1 of FIG. 10 above). This can also be done indirectly, for example by first filling the depression 120 with a removable material 120m such as those described above, followed by the formation of a nanoporous transport-controlling layer 140 and a macroporous layer 150 over the device portion 110 and removable material 120m as shown in FIG. 11, step B1. The removable material 120m is then removed as illustrated in step B2.

The depression 120d (now capped on one end by nanoporous transport-controlling layer 140 and macroporous layer 150) is then filled with a therapeutic agent 120t as shown in step A2 (e.g., using techniques such as those described above in conjunction with FIG. 10, step A1). Finally, an additional layer 170, which may or may not be a nanoporous layer, is provided over the therapeutic-agent-loaded depression 120t and the medical device portion 110 as illustrated in FIG. 11, step A3. Non nanoporous materials for this purpose may be selected from suitable members of the numerous organic and inorganic materials described above.

Finally, in addition to trenches that are all found at a single depth within the substrate, one may also provide trenches that form crisscrossing grids at different depths within the substrate (including submerged trenches, or "veins"), thereby creating interconnected paths for loading and release of drug.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising:
(a) a substrate, (b) a therapeutic-agent-containing region disposed over the substrate, (c) a nanoporous polymeric transport-controlling layer disposed over the therapeutic-agent-containing region that controls transport of the therapeutic agent to an exterior of the device and (d) an outermost macroporous non-polymeric layer disposed over the nanoporous polymeric transport-controlling layer that isolates the nanoporous polymeric transport-controlling layer from surrounding tissue during in-situ delivery of the therapeutic agent.

2. The medical device of claim 1 wherein the therapeutic-agent-containing region comprises a therapeutic agent-containing layer formed over at least one or more portions of the substrate.

3. The medical device of claim 1 wherein the therapeutic-agent-containing region is disposed within one or more depressions in the substrate.

4. The medical device of claim 3 wherein the one or more depressions is filled with a therapeutic agent in pure form.

5. The medical device of claim 3 wherein the one or more depressions is filled with a porous material in which the therapeutic agent is embedded.

6. The medical device of claim 1 wherein the macroporous non-polymeric layer comprises a ceramic material.

7. The medical device of claim 1 wherein the nanoporous polymeric transport-controlling layer is selected from the group consisting of polycarbonate, cellulose acetate and nylon.

8. The medical device of claim 1, wherein said nanoporous polymeric transport-controlling layer comprises a parallel pore structure.

9. The medical device of claim 1, wherein said nanoporous polymeric transport-controlling layer comprises an interconnected pore structure.

10. The medical device of claim 1, wherein said device is selected from catheters, guide wires, balloons, filters, stents, grafts, stent grafts, vascular access ports, embolization devices, myocardial plugs, patches, pacemakers, pacemaker leads, left ventricular assist devices, total artificial hearts, heart valves, vascular valves, anastomosis clips and rings, and tissue engineering scaffolds.

11. The medical device of claim 1, wherein said therapeutic agent is released from said device in accordance with zero-order release.

12. The medical device of claim 1, wherein said therapeutic agent is selected from one or more of the group consisting of anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, TGF-$\beta$ elevating agents, and agents that interfere with endogenous vasoactive mechanisms.

13. The medical device of claim 1, wherein the nanoporous polymeric transport-controlling layer comprises a polymer that is not a biocompatible polymer.

14. The medical device of claim 1, wherein the nanoporous polymeric transport-controlling layer comprises micropores.

15. The medical device of claim 1, wherein said therapeutic agent selected from cytotoxic agents and cytostatic agents.

16. A method of forming the medical device of claim 1 comprising:
(a) arranging the therapeutic-agent-containing region over the substrate, (b) arranging the nanoporous polymeric transport-controlling layer over the therapeutic-agent-containing region and (c) arranging the macroporous non-polymeric layer over the nanoporous polymeric transport-controlling layer.

17. The method of claim 16 wherein the nanoporous polymeric transport-controlling layer is a nanoporous polymeric membrane and the macroporous non-polymeric layer is formed on the nanoporous polymeric membrane to define a bi-layer membrane, and further comprising disposing the bi-layer membrane over the therapeutic-agent-containing region.

18. The method of claim 16 wherein the nanoporous polymeric transport-controlling layer is a nanoporous polymeric membrane and further comprising (d) forming the macroporous non-polymeric layer on a first side of the membrane and (e) applying a therapeutic agent on a second side of the membrane to define a tri-layer membrane, and (f) disposing the tri-layer membrane on the substrate.

19. The method of claim 16 wherein arranging the macroporous non-polymeric layer comprises sputtering nanoparticles onto the nanoporous polymeric transport-controlling layer or wherein arranging the macroporous non-polymeric layer comprises spray depositing a powder suspension onto the nanoporous polymeric transport-controlling layer.

20. The method of claim 19 wherein the sputtering further comprises filtering the nanoparticles so that only nanoparticles having a selected range of dimensions impinge on the nanoporous polymeric transport-controlling layer.

* * * * *